(12) United States Patent
Young et al.

US011468970B2

(10) Patent No.: US 11,468,970 B2
(45) Date of Patent: *Oct. 11, 2022

(54) ALLELOTYPING METHODS FOR MASSIVELY PARALLEL SEQUENCING

(71) Applicant: Battelle Memorial Institute, Columbus, OH (US)

(72) Inventors: Brian A. Young, Columbus, OH (US); Angela T. Minard-Smith, Marysville, OH (US); Esley M. Heizer, Jr., Galloway, OH (US); Daniel M. Bornman, Powell, OH (US); Mark E. Hester, Reynoldsburg, OH (US); Boyu Yang, Charlottesville, VA (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 538 days.

This patent is subject to a terminal disclaimer.

(21) Appl. No.: 13/952,761

(22) Filed: Jul. 29, 2013

(65) Prior Publication Data

US 2015/0032381 A1 Jan. 29, 2015

(51) Int. Cl.
*G16B 30/00* (2019.01)
(52) U.S. Cl.
CPC ................................. *G16B 30/00* (2019.02)
(58) Field of Classification Search
None
See application file for complete search history.

(56) References Cited

PUBLICATIONS

Dollive et al., "A tool kit for quantifying eukaryotic rRNA gene sequences from human microbiome samples", http://genomebiology.com/2012/13/7/R60, 13 pages.
Gymrek et al., "lobSTR: A short tandem repeat profiler for personal genomes", downloaded from genome.cship.org on Sep. 22, 2015, 10 pages.
Gymrek et al., "Supplemental Material for lobSTR: A novel Pipeline for Short Tandem Repeats Profiling in Personal Genomes", 23 pages.
Warshauer et al., "STRait Razor: A length-based forensic STR allele-calling tool for use with second generation sequencing data", Forensic Science International: Genetics 7 (2013) 409-417.
Baum et al., Rapid Analysis of the Short Tandem Repeat HUMTH01 by Capillary Electrophoresis:, BioTechniques, vol. 17, No. 6 (1994), 6 pages.
Planz et al., "Automated analysis of sequence polymorphism in STR alleles by PCR and direct electrospray ionization mass spectrometry", Forensic Science International: Genetics 6 (2012) 594-606.
Schwartz et al., "AMPFLP-Typing of the D21S11 Microsatellite Polymorphism: Allele Frequencies and Sequencing Data in the Austrian Population", 16th Congress of the International Society for Forensic Haemogenetics (Internationale Gesellschaft fur forensische Hamogenetik e.V.), Santiago de Compostela, Sep. 12-16, 1995, 4 pages.
Brinkmann et al., "Population Genetic Comparisons among Eight Populations using Allele Frequency and Sequence Data from Three Microsatellite Loci", Eur J Hum Genet 1996;4:175-182.
Zhou et al., "The HumD21S11 system of short tandem repeat DNA polymorphisms in Japanese and Chinese", Forensic Science International, 86 (1997) 109-118.
Griffiths et al., "New reference allelic ladders to improve allelic designation in a multiple STR system", Int J Legal Med (1998) 111:267-272.
Walsh et al., "Characterisation of variant alleles at the HumD21S11 locus implies unique Australasian genotypes and re-classification of nomenclature guidelines", Forensic Science International 135 (2003) 35-41.
Egyed et al., "Analysis of eith STR loci in two Hungarian populations", Forensic Science International 113 (2000) 25-27.
Schmitt et al., "Detection of ultra-rare mutations by next-generation sequencing", 14508-14513| PNAS| Sep. 4, 2012| vol. 109| No. 36.
Barber et al., "Sequenc analysis and allelic designation of the two short tandem repeat loci D18S51 and D8S1179", Int J Legal Med (1996) 109:62-65.
Walsh et al., "Sequence analysis and characterization of stutter products at the tetranucleotide repeat locus vWA", Nucleic Acids Research, 1996, vol. 24, No. 14 2807-2812.
Levinson et al., "Slipped-Strand Mispairing: A Major Mechanism for DNA Sequence Evolution", MoL Biol. EvoL 4 (3):203-221: 1987.
Murray et al., "The determination of the sequences present in the shadow bands of a dinucleotide repeat PCR", Nucleic Acids Research, 1993, vol. 21, No. 10 2395-2398.
Hauge et al., "A study of the origin of 'shadow bands' seen when typing dinucleotide repeat polymorphisms by the PCR", Human Molecular Genetics, 1993, vol. 2, No. 4 411-415.
Schlotterer et al., "Slippage synthesis of simple sequence DNA", Nucleic Acids Research, vol. 20, No. 2 211-215.
Kircher et al., "Double indexing overcomes inaccuracies in multiple sequencing on the Illumina platform", Nucleic Acids Research, 2012, vol. 40, No. 1, 8 pages.
"DNA recommendations—further report of the DNA Commission of the ISFH regarding the use of short tandem repeat systems", Editorial, Forensic Science International 87 (1997) 179-184.

(Continued)

*Primary Examiner* — Joseph Woitach
(74) *Attorney, Agent, or Firm* — Barnes & Thornburg LLP (57) ABSTRACT

In one illustrative embodiment, an allelotyping method may include selecting a plurality of text strings that each represent a nucleotide sequence that was read by a massively parallel sequencing (MPS) instrument, where the nucleotide sequences represented by the selected plurality of text strings each correspond to a particular locus, comparing the selected plurality of text strings to one another to determine an abundance count for each unique text string included in the selected plurality of text strings, and determining one or more alleles for the particular locus by comparing the abundance count for each unique text string included in the selected plurality of text strings to an abundance threshold.

15 Claims, 5 Drawing Sheets

Specification includes a Sequence Listing.

(56) References Cited

PUBLICATIONS

"Technical Focus, Definition of D19S433 in Life Technologies HID STR Products", Forensic News 2013, one page.

Moller et al., "Different types of structural vaiation in STRs: HumFES/FPS, HumVWA and HumD21S11", Int J Leg Med (1994) 106:319-323.

Cock et al., "The Sanger FASTQ file format for sequences with quality scores, and the Solexa/lllumina FASTQ variants". Nucleic Acids Research, 2010, vol. 38, No. 6, 1767-1771.

Sharma et al., "Spectral Repeat Finder (SRF): identification of repetitive sequences using Fourier transformation", Bioinformatics, vol. 20 No. 9, 2004, pp. 1405-1412.

Gary Benson, "Tandem repeats finder: a program to analyze DNA sequences", Nucleic Acids Research, 1999, vol. 27, No. 2, 573-580.

Sprecher et al., "General Approach to Analysis of Polymorphic Short Tandem Repeat Loci", BioTechniques, vol. 20, No. 2 (1996), 9 pages.

Butler et al., "Reliable genotyping of short tandem repeat loci without an allelic ladder using time-of-flight mass spectrometry", Int J Legal Med (1998) 112:45-49.

Fordyce et al., "Supplementary Material for: High-throughput sequencing of core STR loci for forensic genetic investigations using the Roche Genome Sequencer FLX platform", BioTechniques 51:127-133 (Aug. 2011).

Fordyce et al., "High-throughput sequencing of core STR loci for forensic genetic investigations using the Roche Genome Sequencer FLX platform", BioTechniques 51:127-133 (Aug. 2011).

Fondonm et al., "Analysis of Microsatellite Variation in Drosophila melanogaster with Population-Scale Genome Sequencing", PLos One, Mar. 2012, vol. 7, Issue 3, 9 pages.

Highnam et al., "Accurate human microsatellite genotypes from high-throughput resequencing data using informed error profiles", Nucleic Acids Research, 2013, vol. 41, No. 1, 7 pages.

Nielsen et al., "Genotype and SNP calling from next-generation sequencing data", Nature Reviews|Genetics, vol. 12, Jun. 2011, 9 pages.

"Microsatellite" downloaded from http://en.wikipedia.org/w/index.php?title=Microsatellite&oldid=5 Feb. 7, 2014, 13 pages.

Quail et al., A tale of three next generation sequencing platforms: comparison of Ion Torrent, Pacific Biosciences and Illumina MISeq sequencers:, BMIC Genomics 2012, 13:341, 13 pages.

Reiss et al., "The effect of replication errors on the mismatch analysis of PCR-amplified DNA", Nucleic Acids Research, vol. 18, No. 4, 6 pages.

Butler et al., "High-Throughput STR Analysis by Time-of-Flight Mass Spectrometry", pp. 121-130.

Gymrek et al., "lobSTR: A short tandem repeat profiler for personal genomes", downloaded from genome.cship.org on May 14, 2012, 10 pages.

Bizzaro et al., "Poly: a quantitative analysis tool for simple sequence repeat (SSR) tracts in DNA", BMC Bioinformatics 2003, 4:22, 6 pages.

Gilder et al., "Run-Specific Limits of Detection and Quantitation for STR-based DNA Testing", J Forensic Sci., Jan. 2007, vol. 52, No. 1, 5 pages.

Chen et al., "MfSAT: Detect simple sequence repeats in viral genomes", Bioinformation 6(4): 171-172 (2011).

International Search Report for PCT/US2014/027582, dated Jul. 11, 2014, 14 pages.

"Detection limit" downloaded from Wikipedia Oct. 14, 2015, 4 pages.

Catherine M. Grgicak, "Analytical Thresholds: Determination of Minimum Distinguishable Signals" ISHI 2010 Mixture Workshop, Oct. 11, 2010, 7 pages.

Van Neste et al., "My-Forensic-Loci-queries (MyFLq) framework for analysis of forensic STR data generated by massive parallel serquencing", Forensic Science International, Genetics 9 (2014) 1-8.

International Search Report for PCT/US2015/048082 dated Feb. 17, 2016, 17 pages.

Decision on Appeal issued from United States Patent and Trademark Office for U.S. Appl. No. 14/489,198 on Jul. 18, 2018, 9 pages.

Decision on Appeal issued from United States Patent and Trademark Office for U.S. Patent Application No. 13/834,83C on Jul. 18, 2018, 22 pages.

J. Shendure et al., "Next-generation DNA sequencing," Nature Biotechnology, Oct. 9, 2008, 11 pages.

FIG. 1

| SEQ ID NO. | Sort Rank | Sequence | Read Count | Length | Interpretation |
|---|---|---|---|---|---|
| 1 | 1 | AGATAGATAGATAGATAGATAGATAGATAGATAGAT | 9345 | 9 | True Allele |
| 2 | 2 | AGATAGATAGATAGATAGATAGATAGATAGATAGATAGAT | 8382 | 10 | True Allele |
| 3 | 3 | AGATAGATAGATAGATAGATAGATAGATAGATAGATAGATAGAT | 521 | 11 | +1 Stutter |
| 4 | 4 | AGATAGATAGATAGATAGATAGATAGATAGAT | 494 | 8 | −1 Stutter |
| 5 | 5 | AGATAGATAGATAGATAGATAGATAGATAGATAGATAGATAGATAGAT | 233 | 12 | +2 Stutter |
| 6 | 6 | AGATAGATAGATAGATAGATAGATAGATAGGTAGATAGAT | 34 | 9 | Sequence Error |
| 7 | 7 | AGATAGATAGATAGATAGATAGATAGATAGATAGATAGGT | 30 | 9 | Sequence Error |
| 8 | 8 | AGATAGATAGATAGATAGATAGATAGATAGATAGGTAGATAGAT | 29 | 10 | Sequence Error |
| 9 | 9 | AGATAGATAGATAGATAGATAGATAGATAGATAGATAGGTAGAT | 28 | 10 | Sequence Error |
| 10 | 10 | AGATAGGTAGATAGATAGATAGATAGATAGATAGATAGAT | 27 | 10 | Sequence Error |
| ... | ... | ... | ... | ... | ... |
| 11 | 589 | GATATAT | 1 | 1.3 | Sequence Error |
| 12 | 590 | AGATAGATAGATCGATAGATAGCTAGATAGATCGATAGATAGAT | 1 | 10 | Sequence Error |
| 13 | 591 | AGATAGATAGTTAGATAGATAGTTAGATAGATTAGAT | 1 | 9 | Sequence Error |
| 14 | 592 | AGATAGATAGATAGATGGATAGATAGTAGGTAGATGGATAGAT | 1 | 9 | Sequence Error |
| 15 | 593 | AGATAGATAGATAGATAGATAGATAGATAGATGGTTAGAT | 1 | 8 | Sequence Error |
| 16 | 594 | AGATAGATAGATAGTTAGATAGATAGATAGTTAGTTAGAT | 1 | 10 | Sequence Error |
| 17 | 595 | AGATAGATAGATAGTAGATAGTTAGATAGATAGTTAGATAGAT | 1 | 9 | Sequence Error |
| 18 | 596 | AGATAGATAGATAGATAGATAGATTAGATAGATAGATAGATAGAT | 1 | 11 | Sequence Error |
| 19 | 597 | AGATAGATAGATAGATAGATAGATAGACAGATAGATAGTTAGAT | 1 | 9 | Sequence Error |
| 20 | 598 | AGATAGATAGATAGTAGATAGTTAGATAGATAGTTAGATAGATAGAT | 1 | 10 | Sequence Error |

```
@M:15:0-A3AWP:1:2114:16225:29025 1:N:0:1 file=SEF0.1 caseID=CMH1249 sampleID=87945 labID=OH01 techID=t.johnson
ATTAAgTCGTAA (SEQ ID NO. 21)
+SNP=rs12913832 allele_A=G allele_B=A allele_A_count=19078 allele_B_count=18790 strand=TOP
FFHHGHHHHEH @M:15:0-A3AWP:1:2114:14928:29032 1:N:0:1 file=SEF0.1 caseID=CMH1249 sampleID=87945 labID=OH01 techID=t.johnson
CTCCCaGGGACG (SEQ ID NO. 22)
+SNP=rs1800407 allele_A=A allele_B=G allele_A_count=4799 allele_B_count=38 strand=BOT
F??GGHEHFG1D @M:15:0-A3AWP:1:2114:15986:29000 1:N:0:1 file=SEF0.1 caseID=CMH1249 sampleID=87945 labID=OH01 techID=t.johnson
CTGTCTcTCTGT (SEQ ID NO. 23)
+SNP=unknown allele_A=C allele_B=G allele_A_count=8753 allele_B_count=8051 strand=TOP
AB$6:PHHMMQ
. . . .
```

FIG. 5

SEQUENCE LISTING

```
<160> NUMBER OF SEQ ID NOS: 23

<210> SEQ ID NO 1
<211> LENGTH: 36
<212> TYPE: DNA
<213> ORGANISM: Homo sapiens

<400> SEQUENCE: 1
agatagatag atagatagat agatagatag atagat                            36

<210> SEQ ID NO 2
<211> LENGTH: 40
<212> TYPE: DNA
<213> ORGANISM: Homo sapiens

<400> SEQUENCE: 2
agatagatag atagatagat agatagatag atagatagat                        40

<210> SEQ ID NO 3
<211> LENGTH: 44
<212> TYPE: DNA
<213> ORGANISM: Homo sapiens

<400> SEQUENCE: 3
agatagatag atagatagat agatagatag atagatagat agat                   44

<210> SEQ ID NO 4
<211> LENGTH: 32
<212> TYPE: DNA
<213> ORGANISM: Homo sapiens

<400> SEQUENCE: 4
agatagatag atagatagat agatagatag at                                32

<210> SEQ ID NO 5
<211> LENGTH: 48
<212> TYPE: DNA
<213> ORGANISM: Homo sapiens

<400> SEQUENCE: 5
agatagatag atagatagat agatagatag atagatagat agatagat               48

<210> SEQ ID NO 6
<211> LENGTH: 36
<212> TYPE: DNA
<213> ORGANISM: Homo sapiens

<400> SEQUENCE: 6
agatagatag atagatagat agataggtag atagat                            36

<210> SEQ ID NO 7
<211> LENGTH: 36
<212> TYPE: DNA
<213> ORGANISM: Homo sapiens

<400> SEQUENCE: 7
agatagatag atagatagat agatagatag ataggt                            36

<210> SEQ ID NO 8
<211> LENGTH: 40
<212> TYPE: DNA
<213> ORGANISM: Homo sapiens

<400> SEQUENCE: 8
```

-continued agatagatag atagatagat agatagatag gtagatagat                40

<210> SEQ ID NO 9
<211> LENGTH: 40
<212> TYPE: DNA
<213> ORGANISM: Homo sapiens

<400> SEQUENCE: 9
agatagatag atagatagat agatagatag ataggtagat                40

<210> SEQ ID NO 10
<211> LENGTH: 40
<212> TYPE: DNA
<213> ORGANISM: Homo sapiens

<400> SEQUENCE: 10
agataggtag atagatagat agatagatag atagatagat                40

<210> SEQ ID NO 11
<211> LENGTH: 7
<212> TYPE: DNA
<213> ORGANISM: Homo sapiens

<400> SEQUENCE: 11 gatatat                                                     7

<210> SEQ ID NO 12
<211> LENGTH: 40
<212> TYPE: DNA
<213> ORGANISM: Homo sapiens

<400> SEQUENCE: 12
agatagatcg atagatagct agatagatcg atagatagat                40

<210> SEQ ID NO 13
<211> LENGTH: 36
<212> TYPE: DNA
<213> ORGANISM: Homo sapiens

<400> SEQUENCE: 13
agatagatag ttagatagat agttagatag atagat                    36

<210> SEQ ID NO 14
<211> LENGTH: 36
<212> TYPE: DNA
<213> ORGANISM: Homo sapiens

<400> SEQUENCE: 14
agatagatag atggatagat aggtagatgg atagat                    36

<210> SEQ ID NO 15
<211> LENGTH: 32
<212> TYPE: DNA
<213> ORGANISM: Homo sapiens

<400> SEQUENCE: 15
agatagatag atagatagat agatggttag at                        32

<210> SEQ ID NO 16
<211> LENGTH: 40
<212> TYPE: DNA
<213> ORGANISM: Homo sapiens

```
<400> SEQUENCE: 16
agatagatag ttagttagat agatagatag ttagttagat                40

<210> SEQ ID NO 17
<211> LENGTH: 36
<212> TYPE: DNA
<213> ORGANISM: Homo sapiens

<400> SEQUENCE: 17
agatagatag atagatagtt agttagttag atagat                    36

<210> SEQ ID NO 18
<211> LENGTH: 44
<212> TYPE: DNA
<213> ORGANISM: Homo sapiens

<400> SEQUENCE: 18
agatagatag atagatagtt agatagatag atagatagat agat           44

<210> SEQ ID NO 19
<211> LENGTH: 36
<212> TYPE: DNA
<213> ORGANISM: Homo sapiens

<400> SEQUENCE: 19
agatagatag atagatagac agatagatag ttagat                    36

<210> SEQ ID NO 20
<211> LENGTH: 40
<212> TYPE: DNA
<213> ORGANISM: Homo sapiens

<400> SEQUENCE: 20
agatagatag atagttagat agttagatag atagatagat                40

<210> SEQ ID NO 21
<211> LENGTH: 12
<212> TYPE: DNA
<213> ORGANISM: Homo sapiens

<400> SEQUENCE: 21
attaagtcgt aa                                              12

<210> SEQ ID NO 22
<211> LENGTH: 12
<212> TYPE: DNA
<213> ORGANISM: Homo sapiens

<400> SEQUENCE: 22
ctcccaggga cg                                              12

<210> SEQ ID NO 23
<211> LENGTH: 12
<212> TYPE: DNA
<213> ORGANISM: Homo sapiens

<400> SEQUENCE: 23
ctgtctctct gt                                              12
```

ALLELOTYPING METHODS FOR MASSIVELY PARALLEL SEQUENCING

SEQUENCE LISTING

The instant application contains a Sequence Listing which has been submitted in ASCII format via EFS-Web and is hereby incorporated by reference in its entirety. Said ASCII copy, created on Sep. 5, 2013, is named 920006-225960_SL.txt and is 3,530 bytes in size.

TECHNICAL FIELD

The present disclosure relates, generally, to allelotyping methods and, more particularly, to allelotyping methods for nucleotide sequence data obtained using massively parallel sequencing (MPS).

BACKGROUND

Polymorphic tandem repeats of nucleotide sequences are found throughout the human genome, and the particular combinations of alleles identified by their multiple repeat sites are sufficiently unique to an individual that these repeating sequences can be used in human or other organism identification. These markers are also useful in genetic mapping and linkage analysis, where the tandem repeat sites may be useful for determining, for example, predisposition for disease. Tandem repeats can be used directly in human identity testing, such as in forensics analysis. There are many types of tandem repeats of nucleic acids, falling under the general term variable number tandem repeats (VNTR). For example, minisatellites and microsatellites are VNTRs, and microsatellites include short tandem repeats (STRs).

One application of tandem repeat analysis is in forensics or human identity testing. In current forensics analyses, highly polymorphic STRs are identified using a deoxyribonucleic acid (DNA) sample from an individual and DNA amplification steps, such as polymerase chain reaction (PCR), to provide amplified samples of partial DNA sequences, or amplicons, from the individual's DNA. The amplicons can then be matched by size (i.e., repeat numbers) to reference databases, such as the sequences stored in national or local DNA databases. For example, amplicons that originate from STR loci can be matched to reference STR databases, including the Federal Bureau of Investigation (FBI) Combined DNA Index System (CODIS) database in the United States, or the National DNA Database (NDNAD) in the United Kingdom, to identify the individual by matching to the STR alleles specific to that individual.

Forensic DNA analysis is about to cross a threshold where DNA samples will begin to be analyzed routinely by massively parallel sequencing (MPS), also sometimes referred to in the art as next-generation sequencing. The advent of routine MPS for forensic DNA analysis will create large quantities of nucleotide sequence data that may enable richer exploitation of DNA in forensic applications. Once information is generated on the genetic profile of an individual (e.g., for either forensic investigative purposes or confirmatory matching), the resulting nucleotide sequence data should be formatted for exchange among law enforcement entities. Moreover, forensic analysis requires the preservation of data, including raw data, for evidentiary purposes. Data files created by MPS workflows are typically larger than 1 GB, making them difficult to transmit or store. In addition, these files, while text-based, are not human-readable in any practical sense because of their large size. Thus, other human readable forms of the data from MPS workflows are needed.

SUMMARY

According to one aspect, an allelotyping method may comprise selecting a plurality of text strings that each represent a nucleotide sequence that was read by a massively parallel sequencing (MPS) instrument, where the nucleotide sequences represented by the selected plurality of text strings each correspond to a particular locus, comparing the selected plurality of text strings to one another to determine an abundance count for each unique text string included in the selected plurality of text strings, and determining one or more alleles for the particular locus by comparing the abundance count for each unique text string included in the selected plurality of text strings to an abundance threshold.

In some embodiments, determining the one or more alleles for the particular locus may comprise identifying one or more unique text strings that each represent a nucleotide sequence containing a short tandem repeat (STR). In other embodiments, determining the one or more alleles for the particular locus may comprise identifying one or more unique text strings that each represent a nucleotide sequence containing a single nucleotide polymorphism (SNP).

In some embodiments, comparing the abundance count for each unique text string included in the selected plurality of text strings to the abundance threshold may comprise identifying the unique text string having a highest abundance count from among the selected plurality of text strings. Comparing the abundance count for each unique text string included in the selected plurality of text strings to the abundance threshold may further comprise calculating whether a ratio of the abundance count for each unique text string compared to the highest abundance count exceeds the abundance threshold. The abundance threshold may be a percentage value in the range of 15% to 60%. The abundance threshold may be a percentage value that is configurable by a user.

In some embodiments, the allelotyping method may further comprise receiving a first text-based computer file comprising a plurality of text strings that each represent a nucleotide sequence that was read by the MPS instrument, prior to selecting the plurality of text strings for which the represented nucleotide sequences each correspond to the particular locus, and generating a second text-based computer file comprising each unique text string for which the ratio exceeds the abundance threshold, where a file size of the second text-based computer file is smaller than a file size of the first text-based computer file. The second text-based computer file may comprise one or more unique text strings that each represent a nucleotide sequence determined to be an allele for the particular locus. The file size of the second text-based computer file may be at least ten-thousand times smaller than the file size of the first text-based computer file.

In some embodiments, the steps of (i) selecting the plurality of text strings for which the represented nucleotide sequences each correspond to a particular locus, (ii) comparing the selected plurality of text strings to one another to determine the abundance count for each unique text string included in the selected plurality of text strings, and (iii) determining one or more alleles for the particular locus by comparing the abundance counts to the abundance threshold may be performed for each of a plurality of loci present in a sample that was read by the MPS instrument. Selecting the plurality of text strings for which the represented nucleotide sequences each correspond to one of the plurality of loci may comprise determining whether each of a plurality of text strings generated by the MPS instrument when reading the sample includes text characters that represent a flanking nucleotide sequence associated with a particular locus and selecting a plurality of text strings that include the text characters that represent the flanking nucleotide sequence associated with the particular locus.

In some embodiments, the allelotyping method may further comprise removing the text characters that represent the flanking nucleotide sequence from each of the selected plurality of text strings prior to comparing the selected plurality of text strings to one another to determine the abundance count for each unique text string included in the selected plurality of text strings. The allelotyping method may further comprise removing all text characters that do not represent a short tandem repeat (STR) from each of the selected plurality of text strings prior to comparing the selected plurality of text strings to one another to determine the abundance count for each unique text string included in the selected plurality of text strings.

According to another aspect, a computer-readable medium may store a text-based computer file comprising one or more records. Each of the one or more records may include a first text line, a second text line comprising a text string representing a nucleotide sequence containing a single nucleotide polymorphism (SNP), a third text line comprising a human-readable allele designation for the SNP, and a fourth text line.

In some embodiments, the human-readable allele designation of the third text line may comprise a number of attribute-value pairs that specify a first SNP state, a second SNP state, an abundance count of the first SNP state, an abundance count of the second SNP state, and a strand of the nucleotide sequence represented in the second text line. The human-readable allele designation of the third text line may further comprise an attribute-value pair specifying a reference SNP identifier associated with the nucleotide sequence represented in the second text line.

In some embodiments, the first text line may comprise a unique sequence identifier created by a massively parallel sequencing (MPS) instrument when generating data related to the nucleotide sequence represented in the second text line. The first text line may further comprise forensic metadata specifying one or more of a file format, a unique case identifier, a unique sample identifier, a unique laboratory identifier, and a unique technician identifier. The fourth text line may comprise a text string representing quality scores associated with the nucleotide sequence represented in the second text line.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION OF THE DRAWINGS

While the concepts of the present disclosure are susceptible to various modifications and alternative forms, specific embodiments thereof have been shown by way of example in the figures and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The disclosed embodiments may be implemented, in some cases, in hardware, firmware, software, or any combination thereof. The disclosed embodiments may also be implemented as instructions carried by or stored on a transitory or non-transitory computer-readable storage medium, which may be read and executed by one or more processors. A computer-readable storage medium may be embodied as any storage device, mechanism, or other physical structure for storing or transmitting information in a form readable by a computing device (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

The present disclosure relates to methods of allelotyping loci using an approach based on matching and sorting of the reads generated by an MPS instrument when analyzing a sample. STR loci exist in multiple states, called alleles. STR alleles always differ from one another by nucleotide sequence. In addition, alleles often differ from one another by sequence length. Allelotyping is the process of identifying the one or more alleles present at a particular STR locus in a given sample (by way of example, for a sample from one human, the one allele where the locus is homozygous or the two alleles where the locus is heterozygous). The FBI and other law enforcement agencies around the world have selected about twenty-four specific STR loci for use in forensic DNA analysis applications. These STR loci have been selected because they are highly polymorphic, i.e., multiple alleles exist within the relevant populations. For example, the thirteen STR loci considered by the FBI as their "core" loci each exhibit eight to ten different common allelic forms.

A typical MPS process starts with a DNA sample, which is typically amplified using PCR (however, it will be appreciated that certain DNA samples can also be directly sequenced by MPS instruments without pre-amplification). The output of the MPS process typically takes the form of one or more computer files containing text strings representing the nucleotide sequence that were read by the MPS instrument. The parallel nature of MPS results in numerous replicates of the nucleotide sequence of each allele. This is particularly true when the DNA is pre-amplified by PCR, where the number of replicates of each allelic sequence may number in the tens of thousands. However, both the PCR pre-amplification process and the sequencing process itself have non-trivial error rates. Errors are realized as incorrect nucleotide sequences in many of the copies of the original DNA sequences, i.e., the "true" alleles that existed in the original DNA sample. These sequence errors may act to obscure the nucleotide sequences of the "true" alleles.

Figure 2:
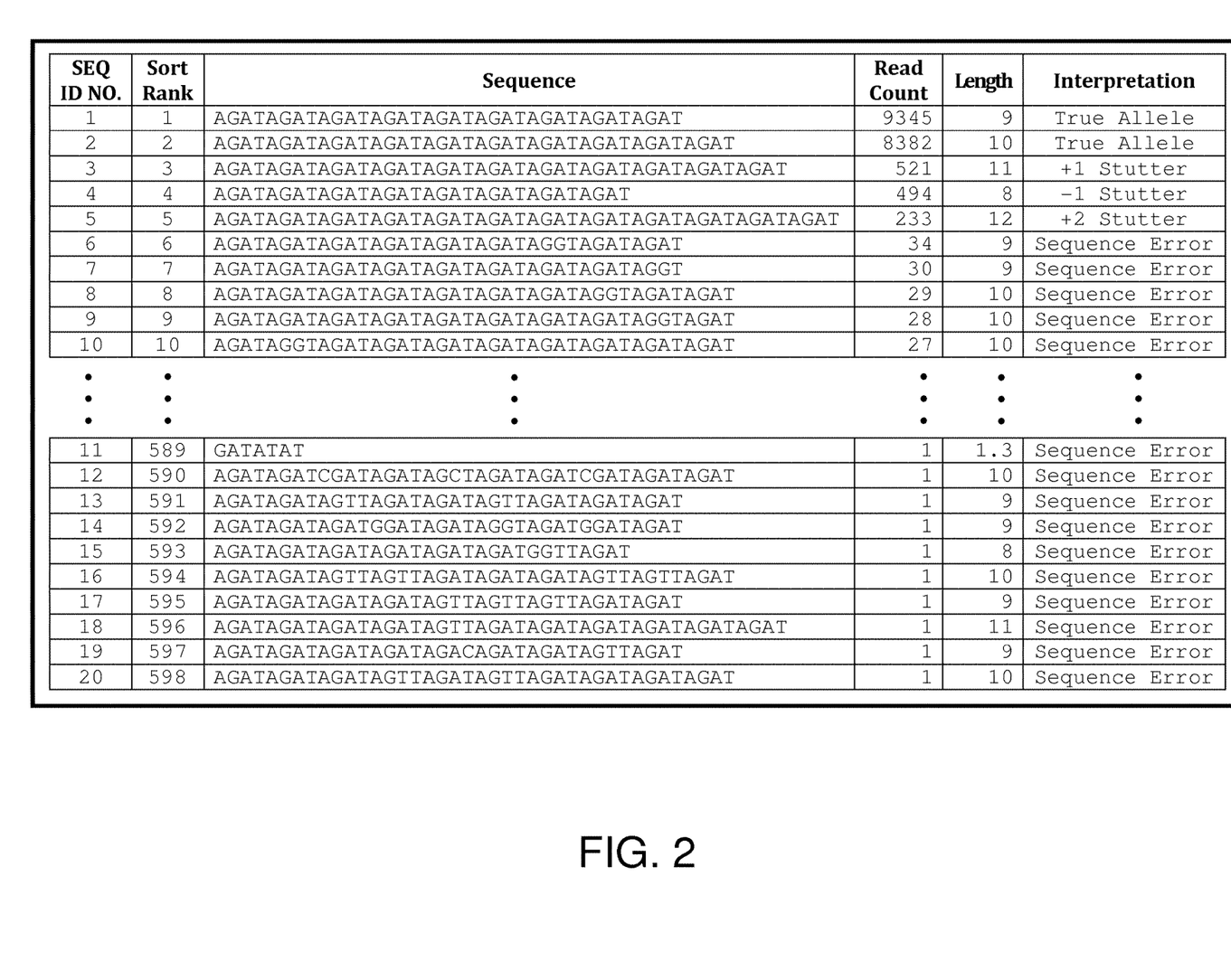
FIG. 2 shows portions of an illustrative table including unique text strings that each represent a nucleotide sequence (SEQ ID NOS 1-20, respectively, in order of appearance) corresponding to a particular locus, in which the unique text strings have been sorted by abundance count using the allelotyping method of FIG. 1.
Figure 3:
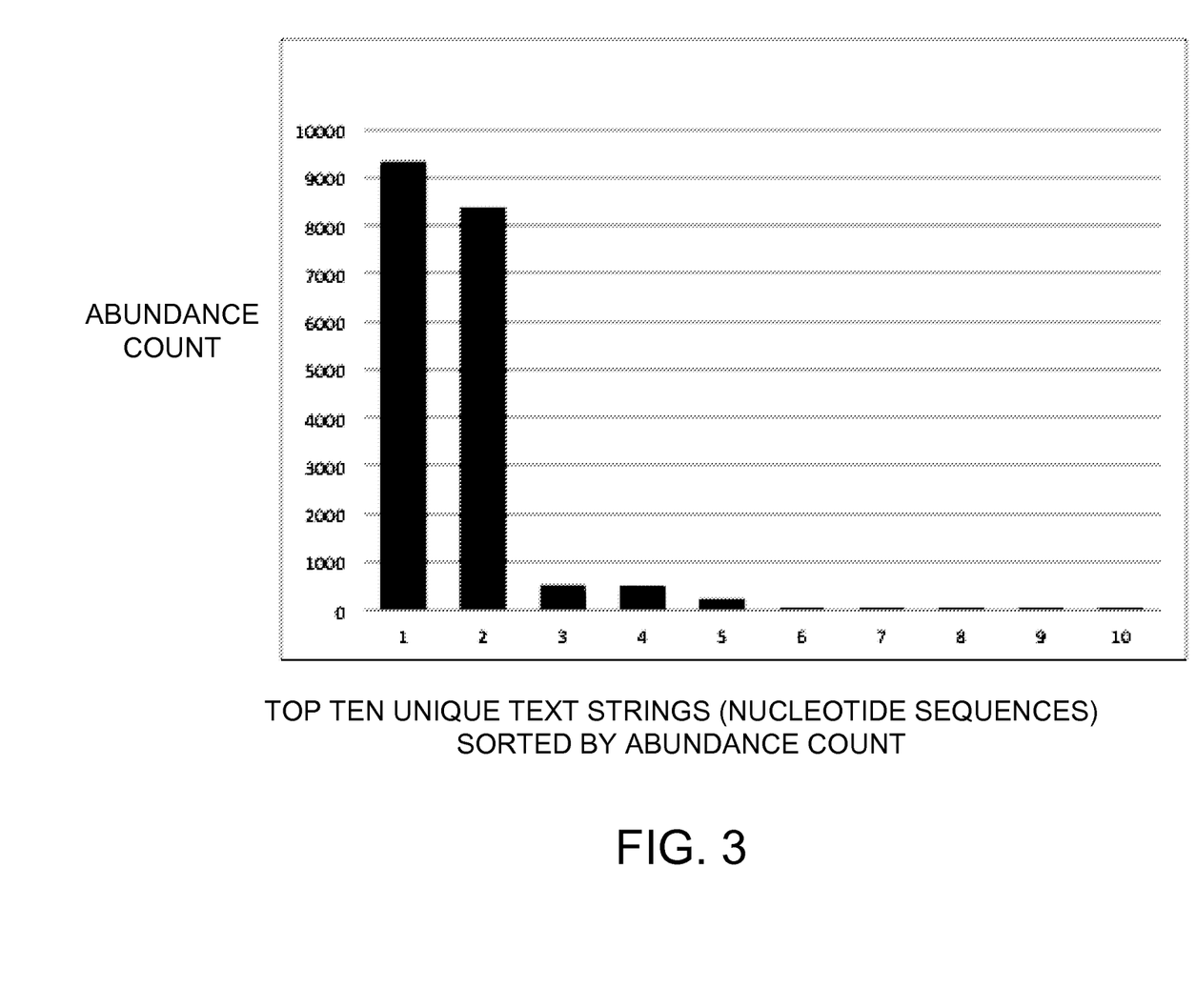
FIG. 3 is a graph of the abundance counts of the top ten unique text strings sorted by abundance from FIG. 2.

The diversity of unique nucleotide sequences generated by a PCR-MPS workflow can be illustrated using an experiment performed on a DNA sample from an anonymous human subject. This anonymous human subject was known to contain allele numbers 9 and 10, (with known sequences $[AGAT]_9$ (SEQ ID NO: 1) and $[AGAT]_{10}$ SEQ ID NO: 2), respectively) at the CSF1PO locus. The MPS instrument returned approximately 20,000 replicate sequences for the two alleles at this locus (i.e., an average of 10,000 replicate sequences per allele). In the absence of error, only these two "true" allele nucleotide sequences would be returned in the data generated by the MPS instrument. However, because of error in the PCR amplification and MPS processes, a total of 598 unique nucleotide sequences were observed. Two correspond to the "true" alleles, and the remaining 596 correspond to method artifacts and sequencing errors. FIG. 2 shows twenty of the 598 unique nucleotide sequences output by the MPS instrument (the top ten most abundant nucleotide sequences, and ten "singleton" nucleotide sequences that each occurred only once), while FIG. 3 shows a graph of the number of reads by the MPS instrument for the top ten most abundant nucleotide sequences. The two most abundant unique nucleotide sequences correspond to the "true" alleles (i.e., allele numbers 9 and 10). The next most abundant unique sequences correspond to PCR stutter artifacts (i.e., the insertion or deletion of repeat motifs in nucleotide sequences due to strand slippage in the PCR process). The less abundant sequences exhibit a wide range of mutations, including sequence truncations and base substitution errors.

Figure 1:
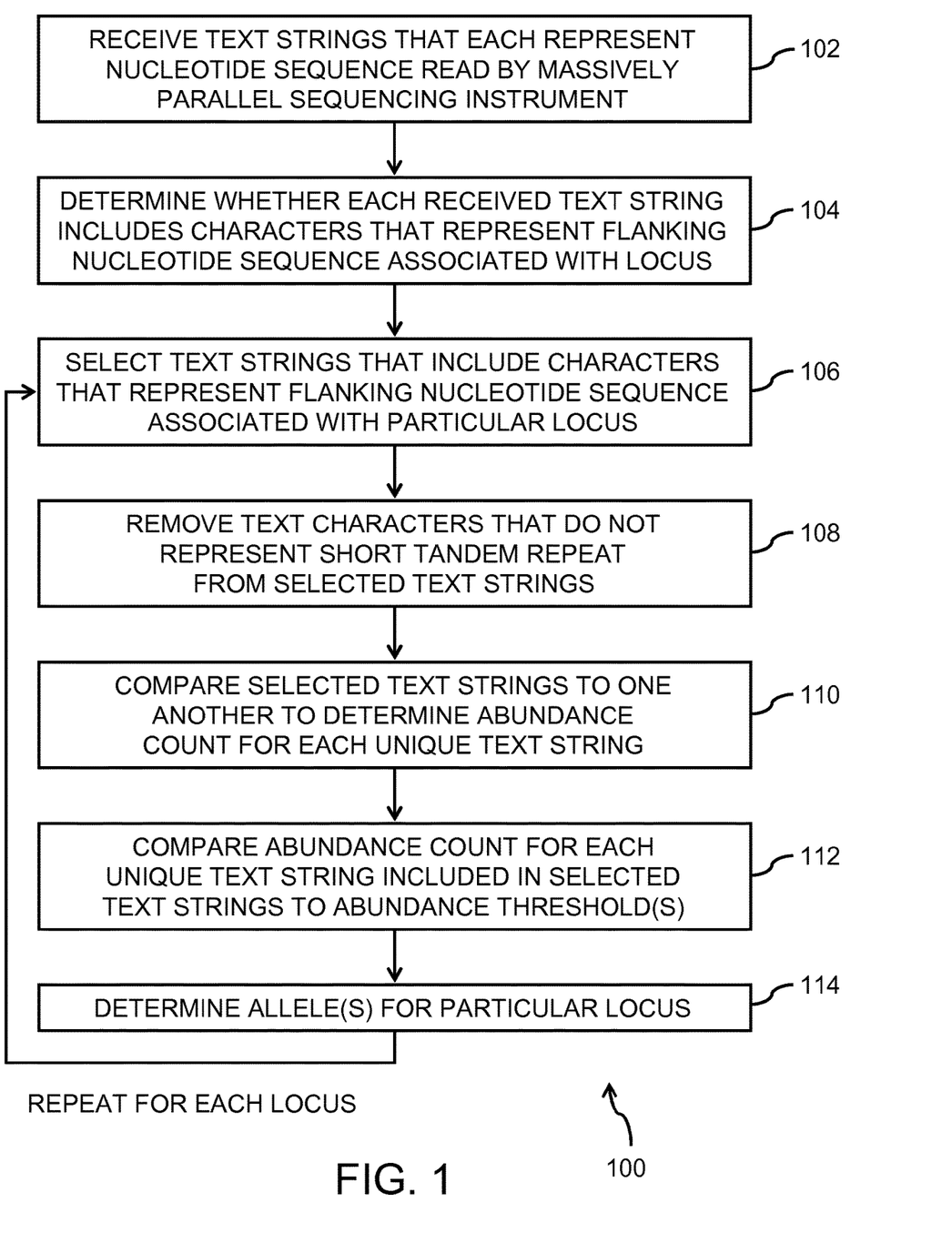
FIG. 1 is a simplified flow diagram illustrating one embodiment of an allelotyping method.

Referring now to FIG. 1, one illustrative embodiment of an allelotyping method 100 that may be used to determine the one or more "true" alleles for each locus of a sample analyzed by an MPS instrument is shown as a simplified flow diagram. In some embodiments, the allelotyping method 100 may be implemented as one or more software routines executed by one or more processors. By way of example, it is contemplated that the allelotyping method 100 may be performed by a processor of the MPS instrument analyzing the sample, in some embodiments, or by a processor of a separate computing device that receives nucleotide sequence data output by the MPS instrument (for instance, in the form of a FASTA or FASTQ file), in other embodiments. The allelotyping method 100 is illustrated in FIG. 1 as a number of blocks 102-114, which will be described in detail below. It will be appreciated that, although the allelotyping method 100 is generally shown in FIG. 1 and described below as having a linear workflow, the allelotyping method 100 may be implemented using any number of workflows (including, by way of example, workflows in which various portions of the allelotyping method 100 are performed in parallel).

The allelotyping method 100 begins with block 102 in which a number of text strings that each represent a nucleotide sequence that was read by an MPS instrument are received. In these text strings, each character represents one base of a nucleotide sequence read by the MPS instrument. As noted above, due to the parallel nature of the MPS process, one sample may result in tens or hundreds of thousands of reads and, hence, associated text strings. Many MPS instruments output this data in files that follow either the FASTA or FASTQ format. As such, in some embodiments of the allelotyping method 100, block 102 may involve receiving such a FASTA or FASTQ file and reading a number of text strings that each represent a nucleotide sequence from that file. In other embodiments, block 102 may involve receiving files in different formats (other than FASTA or FASTQ).

After block 102, the allelotyping method 100 proceeds to block 104 in which a bioinformatic matching procedure is used to determine which reads from the MPS instrument (represented by the received text strings) correspond to one or more particular loci present in the sample. In the illustrative embodiment of block 104, each of the received text strings is evaluated to determine whether it includes characters that represent a known flanking nucleotide sequence associated with a particular locus. The nucleotide sequence of each STR locus is generally flanked, on both the 5' and 3' ends, by particular flanking nucleotide sequences. These complex nucleotide sequences can be rare or unique in the DNA analyzed by the MPS instrument. As such, the presence of one (or both) of these flanking nucleotide sequences may indicate the presence of an STR locus in the nucleotide sequence represented by the text string. It is contemplated that, in other embodiments, the text strings may be searched for other specific nucleotide sequences (e.g., the 5' primer sequences used to PCR amplify each STR locus).

The flanking nucleotide sequences, or other specific nucleotide sequences, used in block 104 may be any length. Longer sequences are more likely to be unique, but increasing length should be balanced against the slower bioinformatic processing inherent to long-sequence matching routines. Moreover, the longer a sequence, the more likely that reads which should contain the sequence will contain an error, reducing the sequence's value as an identifier. In some embodiments, block 104 may reference an external, updatable library of flanking nucleotide sequences (or other specific nucleotide sequences). The text string matching routine used in block 104 can be stringent (e.g., exact character matching) or flexible (e.g., close, overall matching). Block 104 may use any number of bioinformatic approaches, including, but not limited to, string matching routines built into common programming languages (e.g., Java, C++, Perl or Python), regular expression routines built into some programming languages (e.g., Perl) or available as modules for other programming languages, or the like. In some embodiments of block 104, each text string determined to correspond to a particular locus may be grouped or segregated by locus. In other embodiments, each text string determined to correspond to a particular locus may be metadata tagged with that particular locus. In some embodiments, text strings that are not identified as corresponding to any locus (e.g., where the text string does not contain a known flanking nucleotide sequence) may be discarded.

After block 104, the allelotyping method 100 proceeds to block 106 in which the text strings representing nucleotide sequences associated with a particular locus are selected for further processing. In other words, blocks 106-114 of the allelotyping method 100 are performed on a locus-by-locus basis. As indicated in the illustrative embodiment of FIG. 1, blocks 106-114 may be repeated for each locus identified as present in the sample in block 104. In some embodiments, block 106 may involve selecting a locus-specific list containing all of the text strings determined in block 104 to contain characters that represent a known flanking nucleotide sequence associated with a particular locus. In other embodiments, block 106 may involve selecting all text strings assigned a particular metadata tag in block 104.

After block 106, the allelotyping method 100 proceeds to block 108 in which each of the text strings selected in block 106 are trimmed to remove characters that do not represent the nucleotide sequence of interest. For instance, in some embodiments, all characters except those representing an STR may be removed from each of the selected test strings. In other embodiments, all characters except those representing a nucleotide sequence containing a SNP may be removed from each of the selected test strings. In the illustrative embodiment of block 108, the characters representing the 5' and 3' flanking nucleotide sequences (used to identify the text string in block 104), as well as any characters outside of the characters representing the 5' and 3' flanking nucleotide sequences, are removed from each of the selected test strings. After block 108, the text strings contain only the alleles proper, but remain identified with a particular locus (due to the grouping, metadata tagging, or other segregation procedure performed in block 104). It is contemplated that, in some embodiments of the allelotyping method 100, block 108 may be omitted, keeping the characters that do not represent the nucleotide sequence of interest but ignoring those characters in blocks 110-114.

After block 108, the allelotyping method 100 proceeds to block 110 in which each unique text string included in the selected text strings (associated with a particular locus) are grouped and counted. In other words, block 110 determines an abundance count for each nucleotide sequence represented by the selected text strings. In the illustrative embodiment, block 110 involves comparing the selected text strings to one another to determine each unique text string and its abundance in the group of selected text strings. Block 110 may be performed by applying a stringent text string matching routine (e.g., exact character matching) to the selected text strings. As noted above, it is contemplated that string matching routines built into common programming languages (e.g., Java, C++, Perl or Python), regular expression routines built into some programming languages (e.g., Perl) or available as modules for other programming languages, or the like. Block 110 may also involve sorting the unique text strings, each representing a unique nucleotide sequence read by the MPS instrument, into a list according to their abundance counts. FIG. 2 illustrates top and bottom portions of such a list, in which the 598 unique nucleotide sequences output by an MPS instrument and determined to be associated with the CSF1PO locus were sorted by abundance count.

It will be appreciated that the exact-matching scheme in block 110 will result in an abundance count (i.e., a number of occurrences) for each even slightly different nucleotide sequence. For instance, where a text string represents a nucleotide sequence containing a SNP, the allelotyping method 100 will independently count this unique text string (and will not group it with a different text string representing a similar nucleotide sequence not exhibiting the SNP). This approach is quite different from prior alignment-based allelotyping methods, which attempt to identify which reference sequence each portion of nucleotide sequence data most resembles.

After block 110, the allelotyping method 100 proceeds to block 112 in which the abundance count for each unique text string determined in block 110 is compared to one or more abundance thresholds. As noted, while the MPS workflow results in many unique nucleotide sequences for a particular locus, one or two of these nucleotide sequences will be the "true" alleles for that particular locus (in the case of a sample from one human). As explained further below, comparison of each of the abundance counts determined in block 110 to an abundance threshold may allow determination of the one or more alleles for that particular locus. In the illustrative embodiment, block 112 involves identifying the unique text string having the highest abundance count from among the selected text strings. The nucleotide sequence represented by this text string will be one allele for the associated locus, because despite the non-trivial error rates, PCR and MPS workflows exhibit sufficient fidelity to generate correct sequences in abundance. The illustrative embodiment of block 112 also involves calculating a ratio of the abundance count for each unique text string as compared to that highest abundance count. It may then be determined whether the ratio calculated for each unique text string exceeds the abundance threshold(s). In some embodiments of block 112, each abundance threshold may be a predetermined percentage value. For instance, the abundance threshold may be a percentage value in the range of 15% to 60%, as explained further below. In other embodiments, the abundance threshold may be a percentage value that is configurable by a user of the allelotyping method 100.

After block 112, the allelotyping method 100 proceeds to block 114 in which the one or more alleles for the particular locus being considered are determined based on the comparisons performed in block 112. By way of example, where the sample analyzed by the MPS instrument is known to contain DNA from a single human source, the abundance threshold used in block 112 may be set to a percentage value in the range of about 50% to about 60%. It is known that, for sister alleles at a heterozygous locus, the lesser abundant allele will typically have a ratio of about 50-60% or greater to the more abundant allele (i.e., the allele represented by the text string with the highest abundance count). As such, if a second text string is determined in block 112 to have an abundance count exceeding about 50-60% of the highest abundance count, block 114 may conclude that the locus is heterozygous and that the second text string represents the lesser abundant sister allele. Alternatively, if no text string is determined in block 112 to have an abundance count exceeding about 50-60% of the highest abundance count, block 114 may conclude that the locus is homozygous and that the text string with the highest abundance count represents the only allele at that particular locus. As another example, in cases where it is unknown if the sample analyzed by the MPS instrument contained DNA from multiple sources, the abundance threshold used in block 112 may be set to a percentage value of about 15% (or higher). This abundance threshold may capture alleles from a secondary source that is present in a lower amount in the sample, while avoiding detection of artifacts caused by PCR stutter (which tend to be about 4-15% of the corresponding allele abundance count). In yet another embodiment, the abundance threshold might be set to a percentage value of about 4% to capture PCR stutter artifacts but avoid background noise (which tends to be <4% of the highest abundance count).

Figure 4:
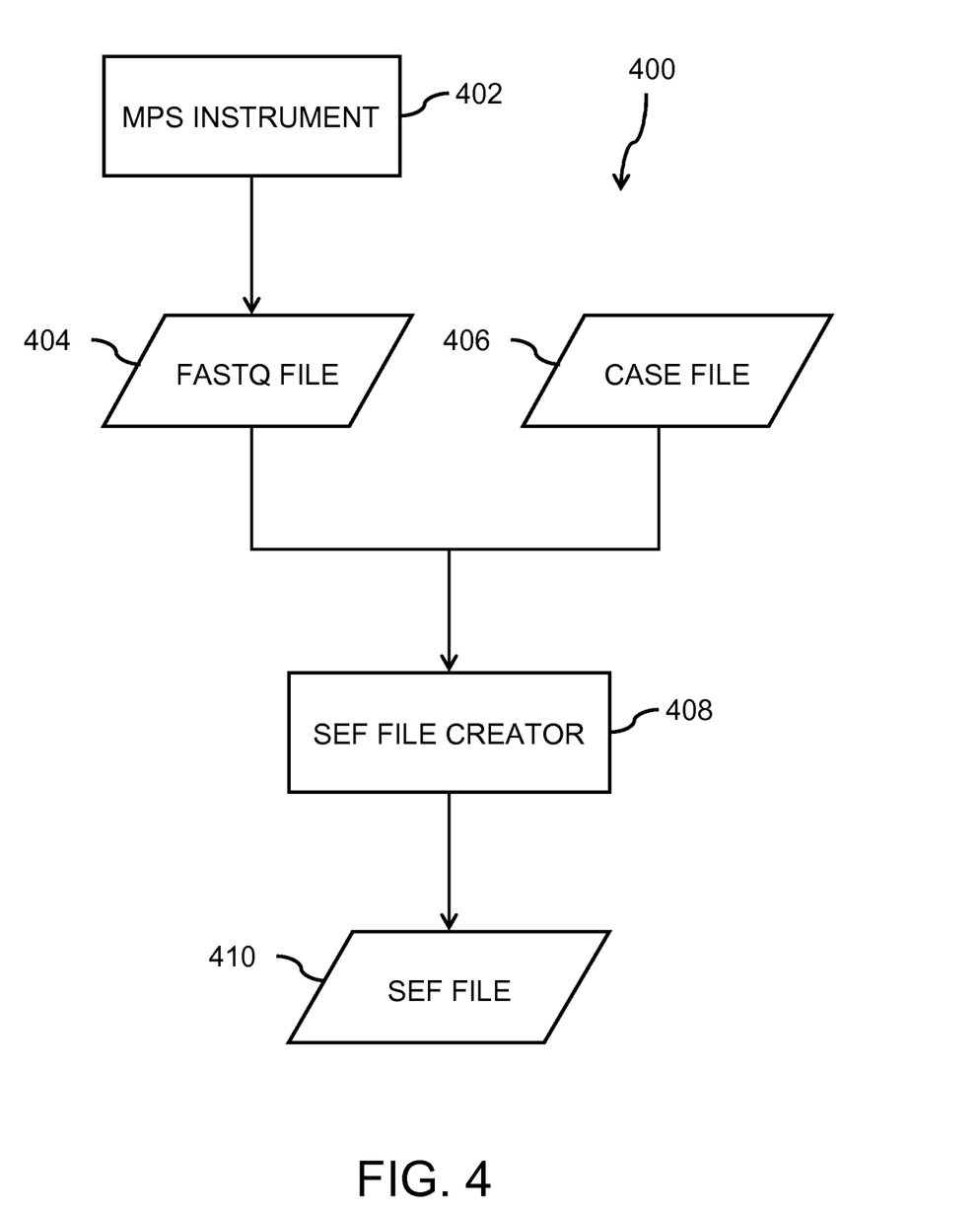
FIG. 4 is a simplified flow diagram illustrating one embodiment of a method of creating a text-based computer file in the Sequence Evidence Format (SEF)

Referring now to FIG. 4, one illustrative embodiment of a method 400 of creating a text-based computer file 410 in a Sequence Evidence Format (SEF) is shown as a simplified flow diagram. Certain illustrative embodiments of the SEF are described in detail in U.S. patent application Ser. No. 13/834,830, filed Mar. 15, 2013, and entitled "Computer Files and Methods Supporting Forensic Analysis of Nucleotides Sequence Data," the entire disclosure of which is incorporated herein by reference (the foregoing application generally referring to the SEF as the "FASTF file format"). Additional illustrative embodiments of the SEF are further described below (with reference to FIG. 5).

The method 400 is intended for use in the forensic DNA analysis process to create an SEF file 410 that may serve as an evidentiary record. As shown in FIG. 4, an SEF file creator 408 may ingest data from at least two different sources. Raw nucleotide sequence data, quality scores associated with the nucleotide sequence data, and instrument-specific metadata may be ingested from a FASTQ file 404 generated by an MPS instrument 402 (and its associated software). Each record of the FASTQ file 404 includes a text string that represents a nucleotide sequence that was read by the MPS instrument 402, with each of the characters of that text string representing an output of a base call algorithm performed by the MPS instrument 402. The SEF file creator 408 may also ingest a case file 406 received from a laboratory case management system. In other embodiments of the method 400, the case management information may be manually input by a user of the MPS instrument 402 via a user interface. Using this input, the SEF file creator 408 may write forensic metadata to each record of the SEF file 410.

The SEF file creator 408 may perform processing on the raw nucleotide sequence data ingested from the FASTQ file 404 when generating the SEF file 410. In the illustrative embodiment of the method 400, the SEF file creator 408 performs the allelotyping method 100 on the nucleotide sequence data in the FASTQ file 404. In this embodiment, block 102 of the allelotyping method 100 involves receiving the FASTQ file 404, which contains a number of text strings that each represent a nucleotide sequence read by the MPS instrument 402. Upon completion of the allelotyping method 100, the SEF file creator 408 may write each unique text string determined in block 112 of the allelotyping method 100 to exceed the abundance threshold to the SEF file 410. In some embodiments, the SEF file creator 408 may write each unique text string determined in block 114 of the allelotyping method 100 to represent an allele for a particular locus to the SEF file 410.

It will be appreciated that, as a result of the allelotyping method 100, the SEF file 410 generated by the SEF file creator 408 may have a file size that is significantly smaller than that of the FASTQ file 404. While the FASTQ file 404 contains an individual, four-line record for every read performed by the MPS instrument 402, the SEF file 410 contains only one four-line record for each "true" allele in the sample (and any other nucleotide sequences of interest). As such, using the allelotyping method 100, the SEF file creator 408 is able to "compress" the FASTQ file 404 into the SEF file 410 while retaining all of the information important for forensic analysis. Table 1 below sets forth five examples of FASTQ files 404 that were processed by the SEF file creator 408 to generate SEF files 410. As can be seen from these five examples, the allelotyping method 100 can produce an SEF file 410 with a file size that is at least 10,000 times smaller than the file size of the source FASTQ file 404.

TABLE 1

| FASTQ File Size (kB) | SEF File Size (kB) | Flank Size (nucleotides) | Min. Stack Coverage | Processing Time (Min.) |
|---|---|---|---|---|
| 1,723,996 | 20 | 10, 10 | 4 | 2:05 |
| 697,339 | 18 | 10, 10 | 4 | 0:45 |
| 697,339 | 12 | 10, 10 | 50 | 0:39 |
| 1,794,807 | 13 | 10, 10 | 50 | 2:04 |
| 1,414,563 | 11 | 10, 10 | 50 | 1:37 |

Figure 5:
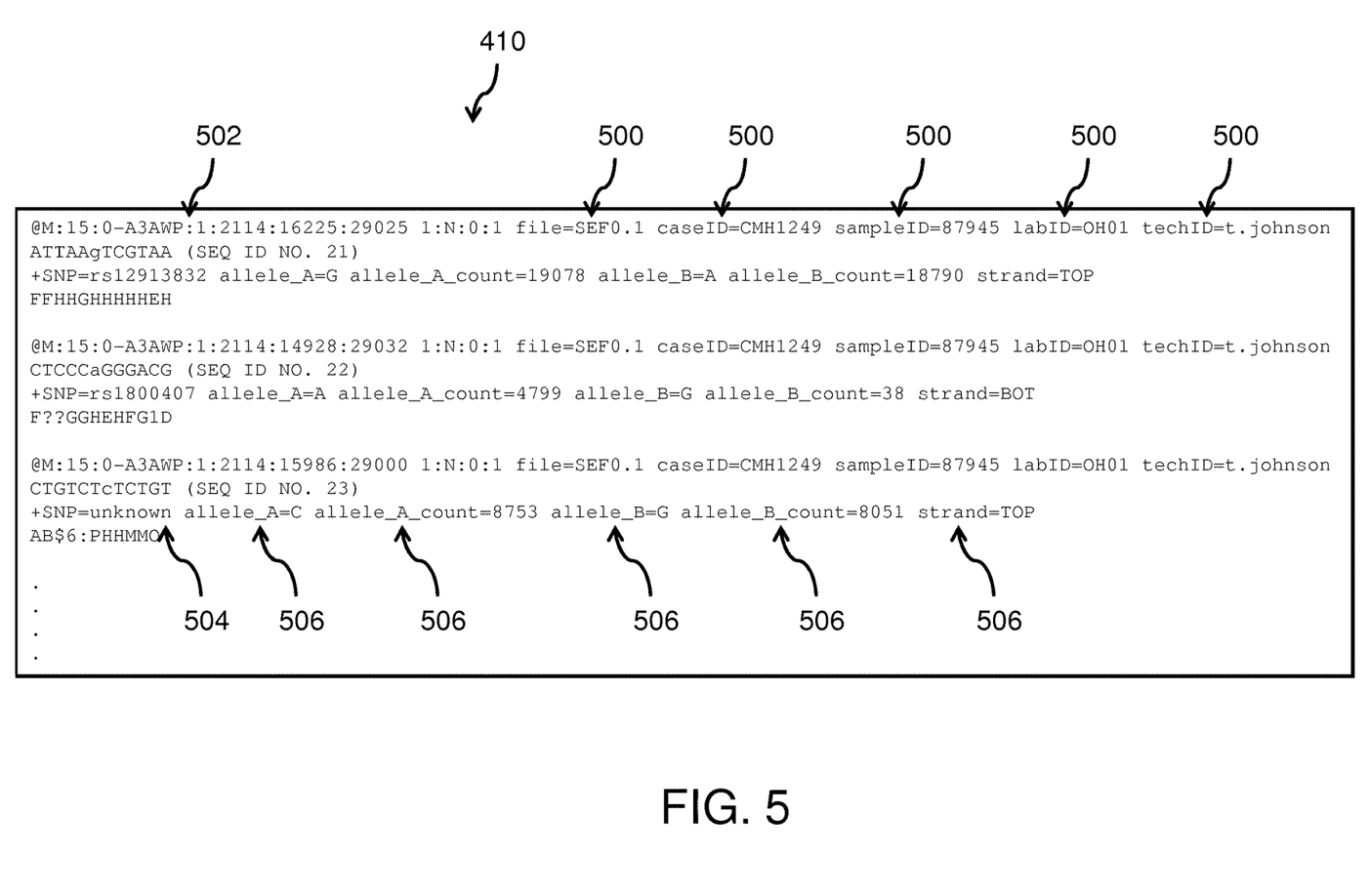
FIG. 5 illustrates a portion of one embodiment of an SEF file comprising human-readable allele designations for several single nucleotide polymorphisms (SNPs) (SEQ ID NOS 21-23, respectively, in order of appearance).

Several records of one illustrative embodiment of an SEF file 410 are illustrated in FIG. 5. Specifically, the illustrative embodiment of the SEF file 410 shown in FIG. 5 comprises data and metadata relating to several nucleotide sequences that contain a SNP. The SEF file 410 of FIG. 5 conforms to the file format specification outlined in Table 2, which references the FASTQ file format specification (the third column denoting several distinguishing features of this SEF file 410, as compared to FASTQ files 404). It will be appreciated that, in other embodiments, SEF files 410 may be formatted according to additional or different specifications than those set forth in Table 2.

TABLE 2

| Line Type | FASTQ | SEF (Differences from FASTQ) |
|---|---|---|
| 1) Title and Description | First character must be "@" Free format field with no length limitation Arbitrary content can be included | The systematic identifier produced by MPS instrument/software may comprise the initial portion of this field Forensic metadata as a series of optional attribute-value pairs |
| 2) Sequence | No specific initial character is required for this line type Any printable character is permitted Upper case, lower case, and mixed case accepted Can be line wrapped | Only International Union of Pure and Applied Chemistry (IUPAC) nucleotide base codes are permitted ("ACTGNURYSWKMBDHVN.-") |

TABLE 2-continued

| Line Type | FASTQ | SEF (Differences from FASTQ) |
|---|---|---|
| 3) End of Sequence | First character must be "+" If the title line is repeated, it must be identical | Content after "+" does not have to match the title line Human-readable allele designation for SNP or STR alleles as a series of optional attribute-value pairs |
| 4) Quality Scores | Accepts printable ASCII characters 33-126 Can be line wrapped Length must be equal to sequence length | Averaged PHRED scores with an ASCII offset of 33 |

Similar to FASTQ files, the SEF file 410 of FIG. 5 comprises a number of records, where each record includes data in four text lines. The second text line of each record contains a text string representing a nucleotide sequence containing a SNP. In some embodiments, this text string in the second line of each record of the SEF file 410 may be an output of the allelotyping method 100 used to identify the SNP alleles. In the illustrative embodiment of FIG. 5, the SNP nucleotide is printed as a lower case character flanked by upper case characters for the remainder of the nucleotide sequence. The fourth text line of each record may contain average quality scores for the nucleotide sequences represented by the text string of the second text line. The first and third text lines of each record may contain metadata related to case management and to evidence preservation.

In some embodiments, the forensic metadata included in the first text line of each record of the SEF file 410 may be in the form of one or more attribute-value pairs 500. In the illustrative embodiment of FIG. 5, the first text line of each record contains several attribute-value pairs 500. In some embodiments, the attribute-value pairs 500 may specify one or more of a file format, a unique case identifier, a unique sample identifier, a unique laboratory identifier, and a unique technician identifier associated with the SEF file 410. Several illustrative attribute-value pairs 500 are set forth in Table 3 below, including possible permissible values and intended purposes. The first text line of each record of the SEF file 410 may also include a unique sequence identifier 502 created by the MPS instrument 402.

TABLE 3

| Attribute | Permissible Values | Purpose |
|---|---|---|
| file | X := [0-9] Y := [0-9] | X refers to major releases and Y to minor releases |
| caseID | [A-Za-z0-9_.:-] | Unique case identity numbers for case management |
| sampleID | [A-Za-z0-9_.:-] | Unique sample identity numbers for case management |
| labID | [A-Za-z0-9_.:-] | Unique laboratory identity numbers for case management |
| techID | [A-Za-z0-9_.:-] | Unique technician identity numbers for case management |

In the illustrative embodiment of FIG. 5, the third text line of each record of the SEF file 410 comprises a human-readable allele designation for the SNP in the form of a number of attribute-value pairs 504, 506. Several illustrative attribute-value pairs 504, 506 that may be used as part of the human-readable allele designation for the SNP are set forth in Table 4 below, including possible permissible values and intended purposes. The human readable allele designation for the SNP of each record strikes a balance between human and computer readability. One attribute-value pair 504 of the human readable allele designation for the SNP may specify a reference SNP identifier, as reported in the National Center for Biotechnology Information (NCBI) SNP database. Where no reference SNP identifier is available, this attribute-value pair 504 may specify "unknown." Additionally, a series of attribute-value pairs 506 of the human readable allele designation for the SNP may specify the state of the allele. For instance, the human readable allele designation may include attribute-value pairs 506 that specify a first SNP state, a second SNP state, an abundance count of the first SNP state, an abundance count of the second SNP state, and a strand of the nucleotide sequence represented in the second text line. In the illustrative embodiment, the series of attribute-value pairs 506 that specify the state of the allele follow the conventions described in Illumina, Inc., "Technical Note: 'TOP/BOT' Strand and 'A/B' Allele," Pub. No. 370-2006-018 (Jun. 27, 2006), the entire disclosure of which is incorporated herein by reference.

TABLE 4

| Attribute | Permissible Values | Purpose |
|---|---|---|
| SNP | [A-Za-z0-9] | Reference SNP identifier, as reported in NCBI SNP database (can be "unknown") |
| allele_A | [G,A,T,C,g,a,t,c] | SNP allele state (following Illumina A/B convention) |
| allele_B | [G,A,T,C,g,a,t,c] | SNP allele state (following Illumina A/B convention) |
| Strand | [A-Za-z] | Strand where SNP is found (following Illumina TOP/BOT convention). |
| allele_A_count | [0-9] | Abundance count for allele_A |
| allele_B_count | [0-9] | Abundance count for allele_B |

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the methods, systems, and articles described herein. It will be noted that alternative embodiments of the methods, systems, and articles of the present disclosure may not include all of the features described yet still benefit from at least some of the advantages of such features. Those of ordinary skill in the art may readily devise their own implementations of the methods, systems, and articles that incorporate one or more of the features of the present disclosure.

The invention claimed is:

1. An allelotyping method comprising:
amplifying one or more nucleotide sequences corresponding to a particular locus using a PCR amplification process to produce an amplified sample, wherein the amplified sample produced comprises the one or more nucleotide sequences that correspond to the particular locus and one or more erroneous nucleotide sequences that do not correspond to the particular locus, wherein the one or more erroneous nucleotide sequences are introduced during the PCR amplification process;

using a massively parallel sequencing (MPS) instrument to read the one or more nucleotide sequences and the one or more erroneous nucleotide sequences of the amplified sample and to generate a plurality of text strings quantifying the reads of the one of the nucleotide sequences and the one or more erroneous nucleotide sequences of the amplified sample;

comparing the plurality of text strings to one another using a text string matching routine to determine an abundance count for each text string included in the plurality of text strings;

distinguishing each text string quantifying one of the nucleotide sequences from each text string quantifying one of the erroneous nucleotide sequences based upon their relative abundance counts; and determining one true allele for the particular locus by identifying the text string having a highest abundance count from among the plurality of text strings.

2. The allelotyping method of claim 1, wherein determining the one true allele for the particular locus comprises identifying a text string from the plurality of text strings that quantifies a nucleotide sequence containing a short tandem repeat (STR).

3. The allelotyping method of claim 1, wherein determining the one true allele for the particular locus comprises identifying a text string from the plurality of text strings that quantifies a nucleotide sequence containing a single nucleotide polymorphism (SNP).

4. The allelotyping method of claim 1, further comprising determining another true allele for the particular locus by identifying another text string from among the plurality of text strings for which a ratio of the abundance count for that text string compared to the highest abundance count exceeds an abundance threshold.

5. The allelotyping method of claim 4, wherein the abundance threshold is a percentage value in the range of 15% to 60%.

6. The allelotyping method of claim 4, wherein the abundance threshold is a percentage value configurable by a user.

7. The allelotyping method of claim 1, further comprising:
receiving a first text-based computer file comprising the plurality of text strings generated by the MPS instrument; and
generating a second text-based computer file comprising the text string identified as representing one true allele for the particular locus, wherein a file size of the second text-based computer file is smaller than a file size of the first text-based computer file.

8. The allelotyping method of claim 7, wherein the second text-based computer file further comprises another text string identified as representing another true allele for the particular locus, a ratio of the abundance count for the another text string as compared to the highest abundance count exceeding an abundance threshold in the range of 15% to 60%.

9. The allelotyping method of claim 7, wherein the file size of the second text-based computer file is at least ten-thousand times smaller than the file size of the first text-based computer file.

10. An allelotyping method comprising:
amplifying one or more nucleotide sequences corresponding to each of a plurality of loci using a PCR amplification process to produce an amplified sample comprising the one or more nucleotide sequences that correspond to each of the plurality of loci, wherein the amplified sample also comprises erroneous nucleotide sequences introduced during the PCR amplification process;

using a massively parallel sequencing (MPS) instrument to read the one or more nucleotide sequences and the erroneous nucleotide sequences of the amplified sample and to generate a plurality of text strings corresponding to each of the plurality of loci, wherein each plurality of text strings quantifies the reads of the one or more nucleotide sequences that correspond to one of the plurality of loci and of associated erroneous nucleotide sequences of the amplified sample; and for each of the plurality of loci, (i) selecting the plurality of text strings corresponding to a selected locus, (ii) comparing the selected plurality of text strings to one another using a text string matching routine to determine an abundance count for each text string included in the selected plurality of text strings, (iii) distinguishing each text string quantifying one of the nucleotide sequences from each text string quantifying one of the erroneous nucleotide sequences based upon their relative abundance counts, and (iv) determining one true allele for the selected locus by identifying the text string having a highest abundance count from among the plurality of text strings corresponding to the selected locus.

11. The allelotyping method of claim 10, wherein selecting the plurality of text strings corresponding to a selected locus comprises determining whether each text string generated by the MPS instrument when reading the amplified sample includes text characters that represent a flanking nucleotide sequence associated with the selected locus.

12. The allelotyping method of claim 11, further comprising removing the text characters that represent the flanking nucleotide sequence from each of the selected plurality of text strings prior to comparing the selected plurality of text strings to one another to determine the abundance count for each text string included in the selected plurality of text strings.

13. The allelotyping method of claim 1, further comprising removing all text characters that do not represent a short tandem repeat (STR) from each of the plurality of text strings prior to comparing the plurality of text strings to one another to determine the abundance count for each text string included in the plurality of text strings.

14. The allelotyping method of claim 1, wherein comparing the plurality of text strings to one another using the text string matching routine comprises determining whether each text character in one text string from the plurality of text strings exactly matches the similarly positioned text character in another text string from the plurality of text strings.

15. The allelotyping method of claim 1, wherein comparing the plurality of text strings to one another using the text string matching routine comprises grouping all occurrences of identical text strings together in a list and counting a number of occurrences of each text string to determine the abundance count for that text string.

* * * * *